(12) United States Patent
Vodanovic

(10) Patent No.: US 7,551,272 B2
(45) Date of Patent: Jun. 23, 2009

(54) METHOD AND AN APPARATUS FOR SIMULTANEOUS 2D AND 3D OPTICAL INSPECTION AND ACQUISITION OF OPTICAL INSPECTION DATA OF AN OBJECT

(75) Inventor: Bojko Vodanovic, Baie d'Urfé (CA)

(73) Assignee: Aceris 3D Inspection Inc., Baie D'Urfé (CA)

( * ) Notice: Subject to any disclaimer, the term of this patent is extended or adjusted under 35 U.S.C. 154(b) by 397 days.

(21) Appl. No.: 11/269,660

(22) Filed: Nov. 9, 2005

(65) Prior Publication Data

US 2007/0103675 A1 May 10, 2007

(51) Int. Cl.
*G01N 21/00* (2006.01)
(52) U.S. Cl. .................. 356/237.1; 356/237.2
(58) Field of Classification Search ......... 382/141–154; 250/559.22–559.48; 356/601–613, 239.3–239.7, 356/237.2–237.5
See application file for complete search history.

(56) References Cited

U.S. PATENT DOCUMENTS

| | | | |
|---|---|---|---|
| 5,406,372 A | 4/1995 | Vodanovic et al. |
| 5,440,391 A | 8/1995 | Smeyers et al. |
| 5,465,152 A | 11/1995 | Bilodeau et al. |
| 5,479,252 A | 12/1995 | Worster et al. |
| 5,580,163 A | 12/1996 | Johnson, II |
| 5,956,134 A | 9/1999 | Roy et al. |
| 6,118,540 A | 9/2000 | Roy et al. |
| 6,134,013 A | 10/2000 | Sirat et al. |
| 6,167,148 A | 12/2000 | Calitz et al. |
| 6,205,238 B1 | 3/2001 | Ma |
| 6,324,298 B1 | 11/2001 | O'Dell et al. |
| 6,547,409 B2 | 4/2003 | Kiest et al. |
| 6,661,515 B2 | 12/2003 | Worster et al. |
| 6,671,397 B1 | 12/2003 | Mahon et al. |
| 6,731,383 B2 | 5/2004 | Watkins et al. |
| 6,750,974 B2 | 6/2004 | Svetkoff et al. |
| 6,765,666 B1 | 7/2004 | Guest et al. |
| 6,771,807 B2 | 8/2004 | Coulombe et al. |
| 6,773,935 B2 | 8/2004 | Watkins et al. |
| 6,778,282 B1 | 8/2004 | Smets et al. |
| 6,820,349 B2 | 11/2004 | Peine |
| 6,826,298 B1 | 11/2004 | O'Dell et al. |
| 6,870,609 B2 | 3/2005 | Watkins et al. |
| 6,882,415 B1 | 4/2005 | Watkins et al. |
| 6,915,006 B2 | 7/2005 | Beaty et al. |
| 6,934,019 B2 | 8/2005 | Geffen et al. |
| 6,937,753 B1 | 8/2005 | O'Dell et al. |
| 6,947,588 B2 | 9/2005 | Sim |
| 6,970,238 B2 | 11/2005 | Gerhard et al. |
| 6,970,287 B1 | 11/2005 | Watkins et al. |

(Continued)

FOREIGN PATENT DOCUMENTS

WO   WO 2006/065437 A2   6/2006

*Primary Examiner*—Gregory J Toatley, Jr.
*Assistant Examiner*—Tri T Ton
(74) *Attorney, Agent, or Firm*—Goudreau Gage Dubuc

(57) ABSTRACT

The present invention relates to optical inspection of manufactured products, such as integrated circuits wafer bumps. There are provided methods and apparatus for acquisition of optical inspection data of said object, as well as for optical inspection and manufacturing of said object. The invention comprises a 2D optical scanning system and a 3D optical scanning system that can have common image trigger control and/or operate simultaneously without interference to have the same field of view.

24 Claims, 4 Drawing Sheets

U.S. PATENT DOCUMENTS

| | | | |
|---|---|---|---|
| 6,974,964 B1 * | 12/2005 | Wang .................... 250/559.29 | |
| 7,019,826 B2 | 3/2006 | Vook et al. | |
| 7,019,841 B2 | 3/2006 | Mathur | |
| 7,023,559 B1 | 4/2006 | Coulombe et al. | |
| 7,024,031 B1 | 4/2006 | Castellanos-Nolasco et al. | |
| 7,034,272 B1 | 4/2006 | Leonard et al. | |
| 7,081,953 B2 | 7/2006 | Uto et al. | |
| 2004/0167402 A1 * | 8/2004 | Jones et al. ................ 600/437 |

* cited by examiner

METHOD AND AN APPARATUS FOR SIMULTANEOUS 2D AND 3D OPTICAL INSPECTION AND ACQUISITION OF OPTICAL INSPECTION DATA OF AN OBJECT

FIELD OF THE INVENTION

The invention relates to optical inspection of manufactured products, such as integrated circuits wafer bumps.

BACKGROUND OF THE INVENTION

Traditionally, in the field of optical inspection of integrated circuits wafer bumps, 2D inspection was carried out first and then 3D inspection was carried out after the first inspection. In this traditional embodiment, the 2D camera system works in a free run mode at the maximum possible speed while the scanning speed is kept constant and in function of the camera speed and the optical field of view. Mainly, the 2D subsystem consisted of one of the following. The first system was a TDI type camera employing a constant light source while scanning speed is tightly controlled so that the resulting image on the TDI sensor travels across the sensor at the sensor shifting speed enabling the light integration over multiple sensor line. This synchronous speed allows, depending on the length of the TDI sensor, much higher sensitivity to the light due to the effective longer exposure (proportional to the number of the TDI sensor lines) while avoiding blurring due to the motion. The second subsystem was an array type camera employing the strobe lighting as the lighting source. The camera controls the strobe by generating the trigger at the end of the previous image transfer and before the next image transfer in a sequence. Provision must be made to store encoder position at the time of the exposure (strobe).

Processing sequentially the 2D and 3D inspections is a source of technical difficulties, such as inaccurate corresponding between 2D and 3D images associated with a same field of view. Besides, proceeding sequentially with the 2D and 3D inspections is a source of important time consumption in the process of wafer bump inspection.

SUMMARY OF THE INVENTION

It is therefore an object of the present invention to provide methods and apparatus for simultaneous 2D and 3D optical inspection and acquisition of optical inspection data of an object, which overcome the above drawbacks.

According to one aspect of the invention, profile line data acquisition of the 3D optical scanning system and 2D image acquisition of the 2D optical scanning system are triggered automatically at different intervals as a function of a common relative movement between the 3D and 2D systems and the object.

According to another aspect of the invention, a 3D model of the object is generated using the profile line data obtained using a 3D system and at least one 2D image from a 2D system.

According to another aspect of the invention, a 2D imaging system operates with a 3D imaging system with a common field of view by using optically separable illumination and filtering such that image acquisition is simultaneous without interference.

According to further aspect of the invention, there is provided an apparatus for optical inspection and acquisition of optical inspection data of an object. The apparatus comprises a 2D optical scanner for 2D image acquisition of the object, a 3D optical scanner for profile line data acquisition of the object, a scanning motion controller having motion encoder output signal, a trigger controller generating a first trigger signal controlling the 2D optical scanner and a second trigger signal controlling the 3D optical scanner at different intervals as function of the encoder output signal.

Applicant has found that by using methods or an apparatus as defined above, it is possible to carry out simultaneous 2D and 3D scanning of a same field of view of an object without image crossover, reducing in this way the image processing time and enhancing the quality of image.

In the methods of the present invention, the 2D and 3D optical scanning systems preferably use optically separable illumination and filtering such that image acquisition is simultaneous without interference.

The 2D optical scanning system uses preferably a 2D camera and the triggering can comprise triggering the 2D optical scanning system to acquire 2D images with overlap.

In this last case, these 2D images with overlap can be stitched together to provide a single 2D image of the object.

The 2D optical scanning system can also be triggered once to image the object, the object being within a field of view of the 2D optical scanning system.

In the methods of the present invention, providing the 2D and 3D optical scanning systems preferably comprise arranging the systems to have a same field of view.

In the methods of the present invention, orientation line of the 2D optical scanning system preferably forms approximately 90 degrees with orientation line of motion of the object, the 3D optical system orientation line preferably forms approximately 45 degrees with the orientation line of the 2D optical scanning system and orientation line of a plane light projector preferably forms approximately 45 degrees with the orientation line of the 2D optical scanning system.

Besides, a strobe light preferably surrounds the field of view.

In the methods of the present invention, the object is preferably an integrated circuit wafer bump.

BRIEF DESCRIPTION OF THE DRAWINGS

Further features and advantages of the invention will become more readily apparent from the following detailed description of the invention as illustrated by way of examples in the appended drawings wherein.

DETAILED DESCRIPTION OF THE INVENTION

Figure 1:
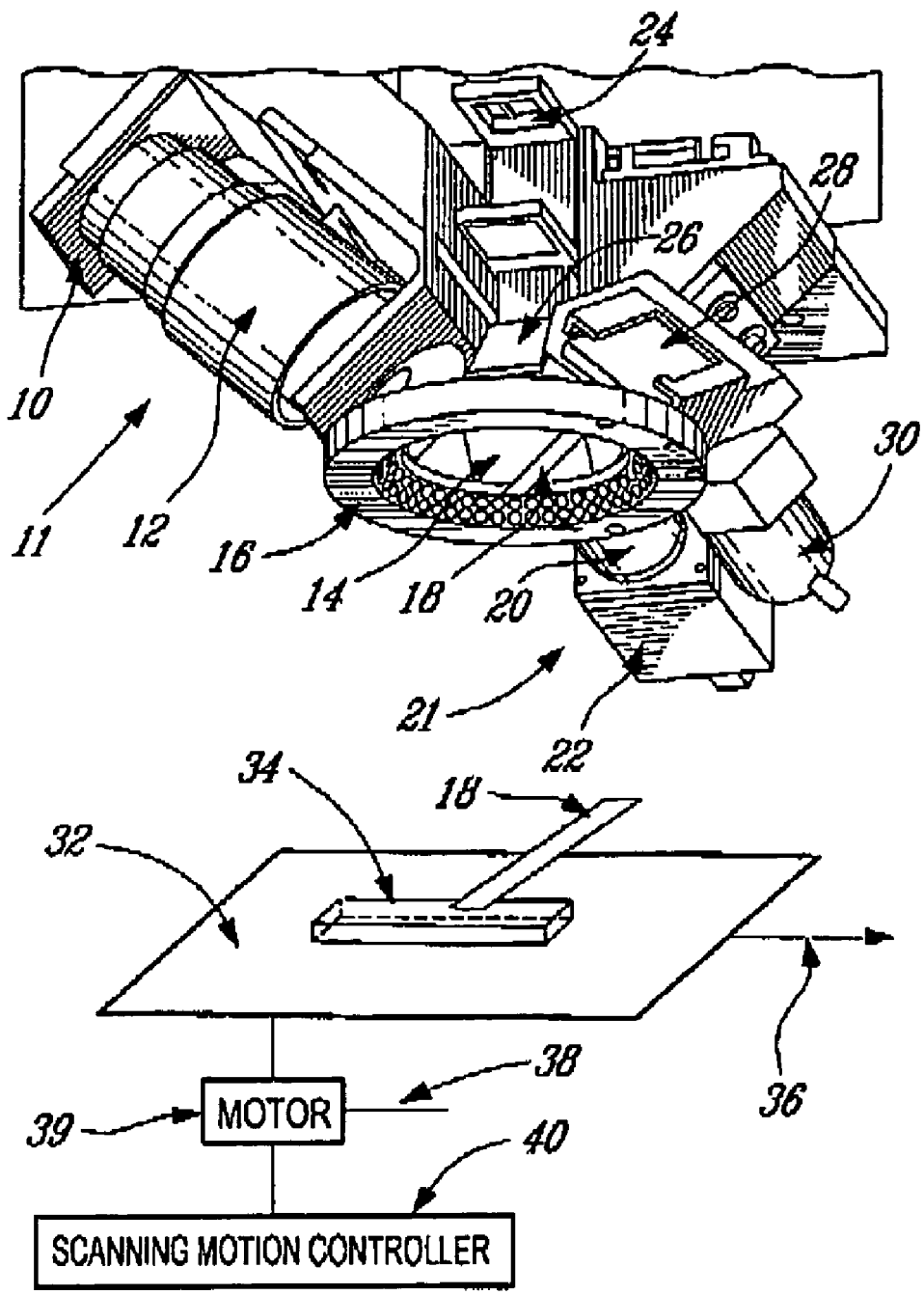
FIG. 1 is a view of a wafer bump optical inspection system wherein the 2D and 3D optical scanning are carried out simultaneously without interference.
Figure 4:
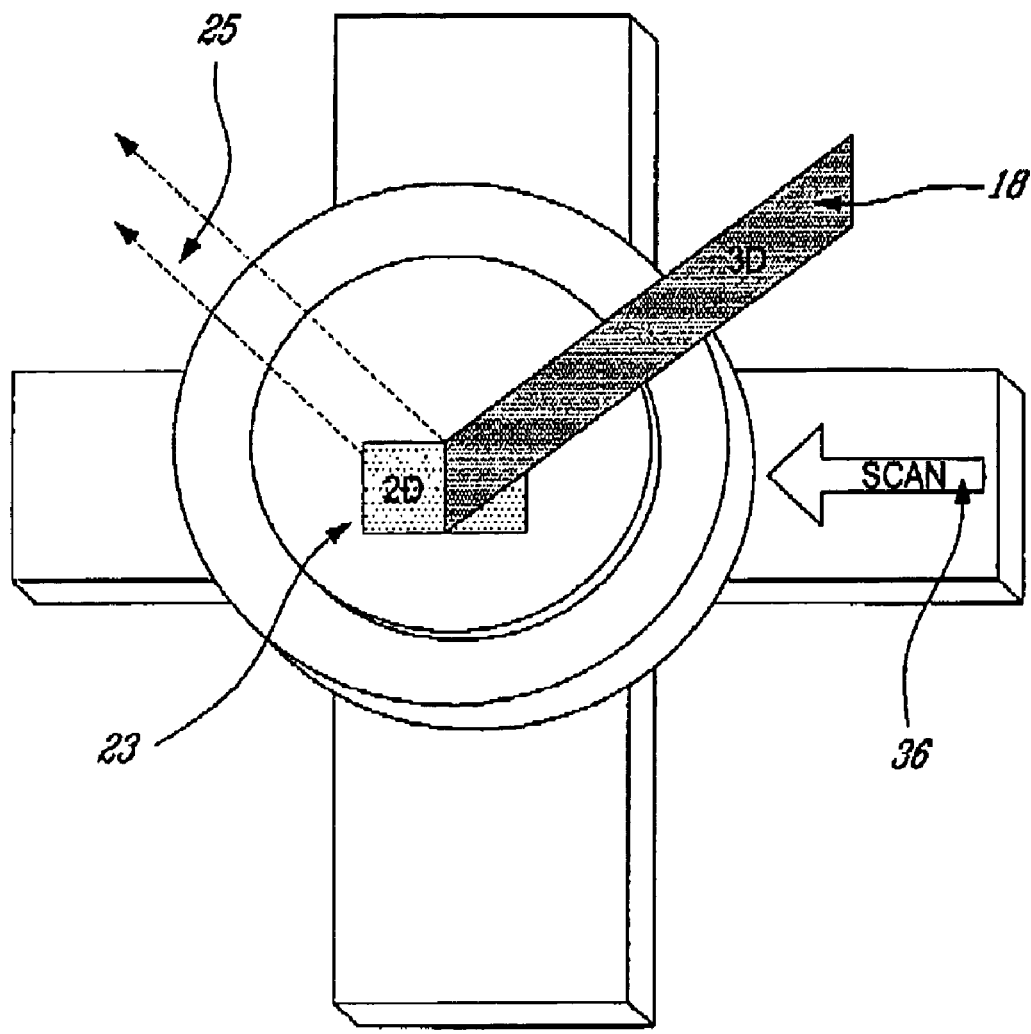
FIG. 4 is a view showing fields of view of the 2D and 3D scanning systems of a wafer bump optical inspection system wherein the 2D and 3D optical scanning are carried out simultaneously without interference.

Referring first to FIG. 1 and FIG. 4, there is shown an optical inspection system wherein the 2D and 3D optical scanning are carried out simultaneously without interference. First, the object being inspected, in the embodiment shown a wafer having bumps, 34 is deposed on a mobile stage 32 that moves with a given speed in a predetermined direction 36, so that the object being inspected 34 passes in the 2D scanning system field of view 23 and in the 3D scanning system field of view 25. The mobile stage 32 is linked to a motor 38 that is controlled by a scanning motion controller 40. Controller 40 controls the speed of the mobile stage 32 as a function of the scan resolution.

The optical inspection system comprises a 2D scanning system 21 for 2D image acquisition and a 3D scanning system 11 for profile line data acquisition. In the 2D scanning system 21, a mirror 26 reflects the image of the object being inspected 34 inside a 2D lens 20 that, in turn, conveys the reflected image inside a 2D camera 22 equipped with a laser-blocking filter. In blocking laser radiation, this filter makes it possible for the 3D scanning system to work simultaneously with the 2D scanning system without interfering the 2D image acquisition.

In the 3D scanning system 11, a laser projector 30 projects a plane laser beam 18 on the object being inspected 34 and a 3D lens 12 acquires the reflected laser beam and conveys it inside a 3D camera 10 that measures the profile line height of the object being inspected 34. The 3D camera 10 comprises a filter which blocks all the other light except the laser, such that it is possible for the 2D scanning system 21 to work simultaneously with the 3D scanning system 11 without interfering the profile line data acquisition. Moreover, the optical inspection system comprises three lights to enhance image acquisition quality, a top light 24, a side light 14 and a strobe ring light 16.

Figure 2:
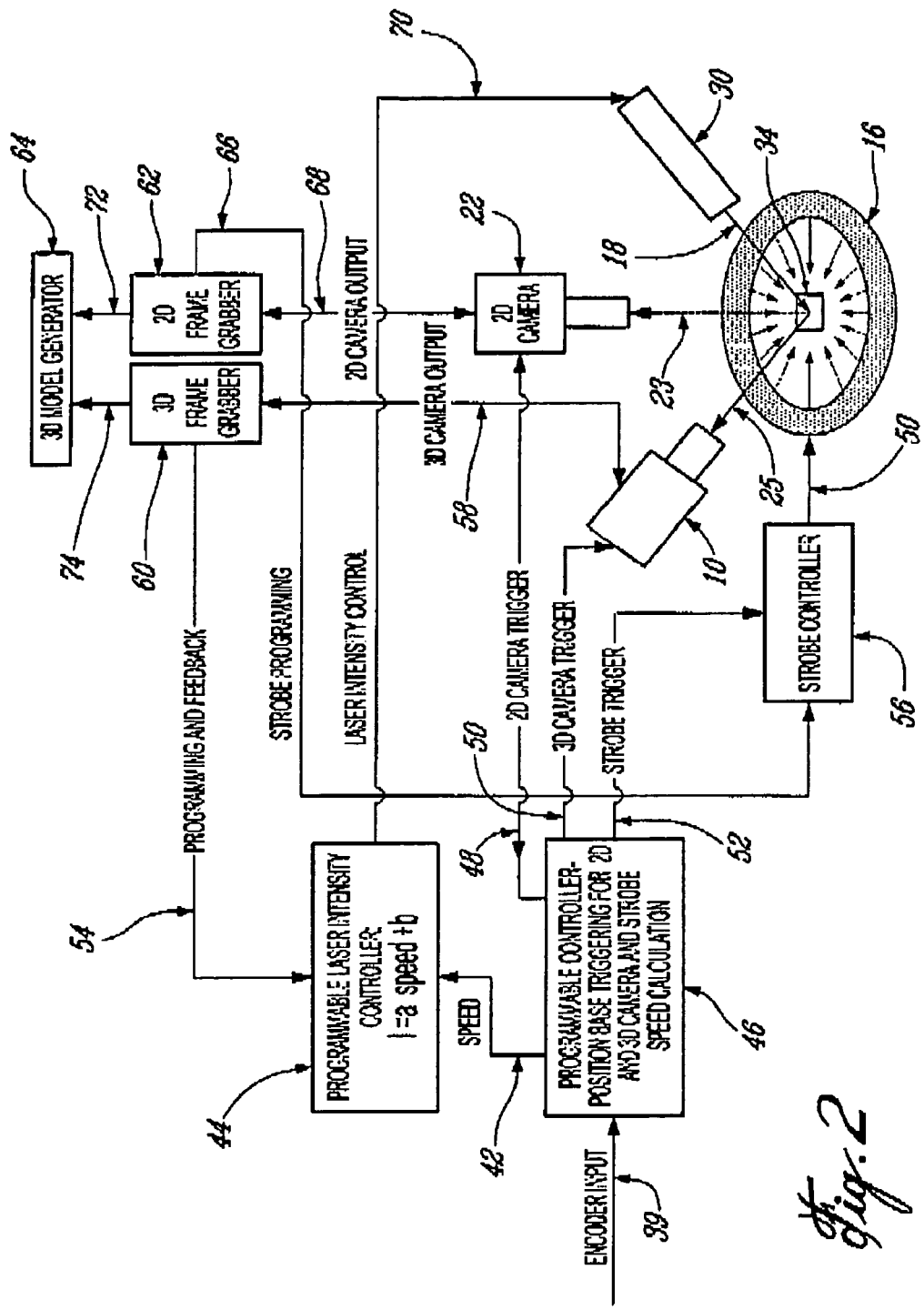
FIG. 2 is a block diagram showing the main parts of a wafer bump optical inspection system wherein the 2D and 3D optical scanning are carried out simultaneously without interference.
Figure 3:
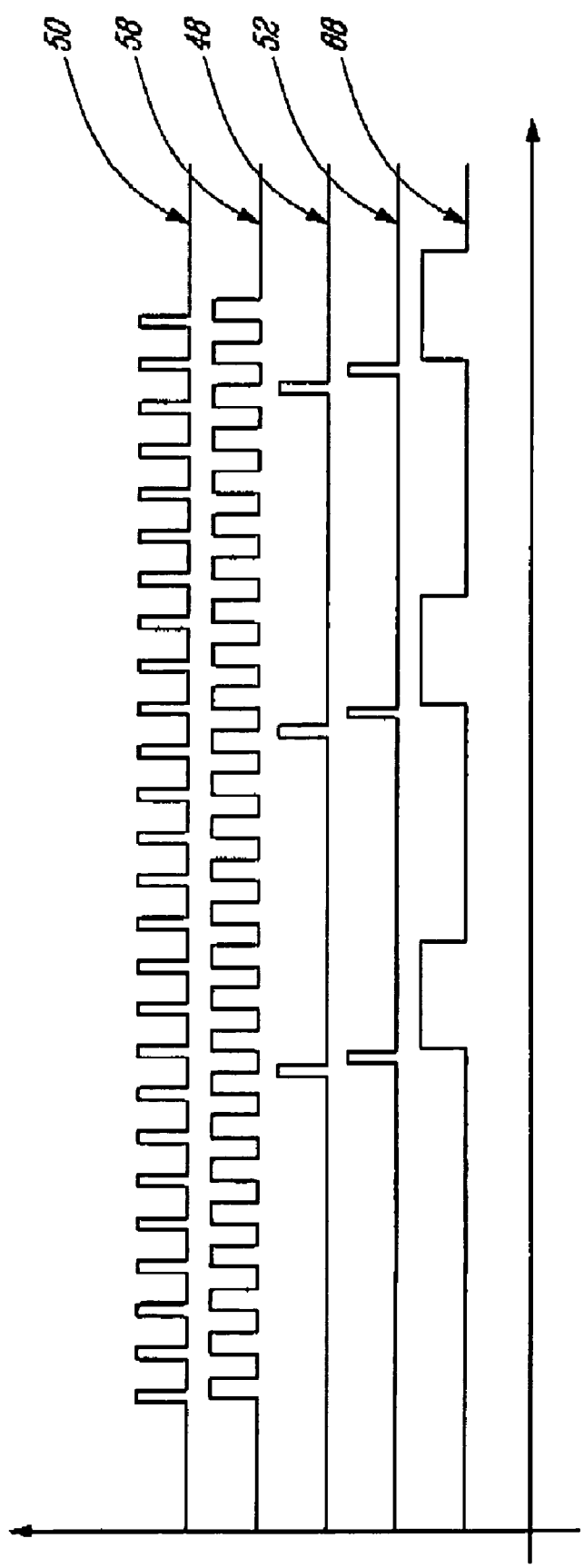
FIG. 3 is a signal chart showing relation between the different main signals of a wafer bump optical inspection system wherein the 2D and 3D optical scanning are carried out simultaneously without interference.

As shown in FIG. 2 and FIG. 3, the main components of the wafer bump optical inspection system are synchronized between each other using electrical signals. An encoder input signal 39 is first sent by the motor 38 to the programmable controller 46 so that it calculates the speed of the object being inspected 34 and, dependently on its position, triggers at different temporal intervals the 2D camera 22, the 3D camera 10 and the strobe light 16. The programmable controller 46 sends a speed signal 42 to the programmable laser intensity controller 44 indicating the speed of the object being inspected 34, a 2D camera trigger signal 48 to the 2D camera 22 such that the latter is triggered upon receiving a high level signal, a 3D camera trigger signal 50 to the 3D camera 10 such that it is triggered upon receiving a high level signal and a strobe trigger signal 52 to the strobe controller 56. Upon receiving the speed information, the programmable laser intensity controller 44 uses this information to calculate the appropriate intensity of the laser beam 18 projected on the object being inspected 34 and sends a laser intensity control signal 70 to the laser projector 30 so that it adjusts its intensity.

Upon triggering the 2D camera 22, it acquires the 2D image of the object being inspected 34 and sends it via the 2D camera output signal 68 for storage in the 2D frame grabber 62. In the same way, upon triggering the 3D camera 10, it acquires the profile line data of the object being inspected 34 and sends it via the 3D camera output signal 58 for storage in the 3D frame grabber 60. Upon acquiring a 2D image of the object being inspected 34, the 2D frame grabber 62 sends a strobe programming signal 66 to the strobe controller 56 indicating acquisition of a 2D image. Then, according to the state of the two received signals, the strobe trigger signal 52 and the Strobe Programming Signal 66, the Strobe Controller 56 triggers the strobe light 16, such that the trigger generation occurs at the end of the previous image acquisition and before the next image acquisition.

Finally, the profile line data and the 2D image of the object being inspected 34 are sent to the 3D Model Generator 64, respectively via the Profile Line Data Output Signal 74 and the 2D image output Signal 72, so that a 3D model can be generated.

While the invention has been described with particular reference to the illustrated embodiment, it will be understood that numerous modifications thereto will appear to those skilled: in the art. Accordingly, the above description and accompanying drawings should be taken as illustrative of the invention and not in a limiting sense.

What is claimed is:

1. A method for acquiring optical inspection data of an object, the method comprising:
   providing a 3D optical scanning system for obtaining profile line data of said object;
   providing a 2D optical scanning system for obtaining at least one 2D image of said object;
   providing relative movement between said object and simultaneously said 2D optical scanning system and said 3D optical scanning system; and
   triggering profile line data acquisition of said 3D optical scanning system and 2D image acquisition of said 2D optical scanning system automatically at different intervals as a function of said relative movement wherein said 2D optical scanning system and said 3D optical scanning system use optically separable illumination and filtering such that a plurality of images representing said profile line data are acquired during an interval within which one of said 2D image is being acquired without interference.

2. The method as claimed in claim 1, wherein said object is an integrated circuit wafer bump.

3. The method as claimed in claim 1, wherein said object is an integrated circuit wafer bump.

4. The method as claimed in claim 1, wherein said 2D optical scanning system is triggered once to image said object, said object being within a field of view of said 2D optical scanning system.

5. The method as claimed in claim 1, wherein said steps of providing said 2D and 3D optical scanning systems comprise arranging said systems to have a same field of view.

6. The method as claimed in claim 5, wherein orientation line of said 2D optical scanning system forms approximately 90 degrees with orientation line of motion of said object, said 3D optical system orientation line forms approximately 45 degrees with said orientation line of said 2D optical scanning system and orientation line of a plane light projector forms approximately 45 degrees with said orientation line of said 2D optical scanning system.

7. The method as claimed in claim 6, wherein said object is an integrated circuit wafer bump.

8. The method as claimed in claim 6, wherein said field of view is illuminated by a strobe ring light for acquiring said 2D images.

9. A method for optical inspection of an object, the method comprising:
   providing a 3D optical scanning system for obtaining profile line data of said object;
   providing a 2D optical scanning system for obtaining at least one 2D image of said object;
   providing relative movement between said object and simultaneously said 2D optical scanning system and said 3D optical scanning system;
   optically separating said 2D optical scanning system from said 3D optical scanning system:
   repeatedly triggering profile line data acquisition by said 3D optical scanning system during intervals of 2D image acquisition by said 2D optical scanning system, wherein said profile line data acquisition and said 2D image acquisition are triggered automatically at different programmable position intervals as a function of said relative movement; and generating a 3D model of said object using said profile line data and said at least one 2D image.

10. The method as claimed in claim 9, wherein said object is an integrated circuit wafer bump.

11. The method as claimed in claim 9, wherein said 2D optical scanning system and said 3D optical scanning system use optically separable illumination and filtering such that image acquisition is simultaneous without interference 12. The method as claimed in claim 11, wherein said object is an integrated circuit wafer bump.

13. The method as claimed in claim 9, wherein said 2D optical scanning system is triggered once to image said object, said object being within a field of view of said 2D optical scanning system.

14. The method as claimed in claim 9, wherein said steps of providing said 2D and 3D optical scanning systems comprise arranging said systems to have a same field of view.

15. The method as claimed in claim 14, wherein orientation line of said 2D optical scanning system forms approximately 90 degrees with orientation line of motion of said object, said 3D optical system orientation line forms approximately 45 degrees with said orientation line of said 2D optical scanning system and orientation line of a plane light projector forms approximately 45 degrees with said orientation line of said 2D optical scanning system.

16. The method as claimed in claim 15, wherein said object is an integrated circuit wafer bump.

17. A method for manufacturing a product, the method comprising:

providing a 3D optical scanning system for obtaining profile line data of said product;

providing a 2D optical scanning system for obtaining at least one 2D image of said product;

providing relative movement between said product and simultaneously said 2D optical scanning system and said 3D optical scanning system;

optically separating said 2D optical scanning system from said 3D optical scanning system:

repeatedly triggering profile line data acquisition by said 3D optical scanning system during intervals of 2D image acquisition by said 2D optical scanning system, wherein said profile line data acquisition and said 2D image acquisition are triggered automatically at different programmable position intervals as a function of said relative movement;

generating a 3D model of said product using said profile line data and said at least one 2D image;

determining from said 3D model a fitness of said product; and recycling or releasing said product as a function of said fitness.

18. The method as claimed in claim 17, wherein said product is an integrated circuit wafer whose fitness is determined by a fitness of bumps thereon.

19. An apparatus for optical inspection and acquisition of optical inspection data of an object, the apparatus comprising:

a 2D optical scanner for 2D image acquisition of said object;

a 3D optical scanner for profile line data acquisition of said object;

a scanning motion controller having motion encoder output signal; and a trigger controller generating a first plurality of trigger signals controlling said 2D optical scanner and a second plurality of trigger signals controlling said 3D optical scanner at different intervals as function of said encoder output signal wherein said 2D optical scanner and said 3D optical scanner use optically separable illumination and filtering such that a plurality of images representing said profile line data are acquired during an interval within which said 2D image is being acquired without interference.

20. The apparatus as claimed in claim 19, wherein said object is an integrated circuit wafer bump.

21. The apparatus as claimed in claim 19, wherein said object is an integrated circuit wafer bump.

22. The apparatus as claimed in claim 19, wherein said 2D optical scanner is triggered once to image said object, said object being within a field of view of said 2D optical scanner.

23. The apparatus as claimed in claim 19, wherein said 2D and 3D optical scanners are arranged in such a way to have a same field of view.

24. The apparatus as claimed in claim 23, wherein orientation line of said 2D optical scanner forms approximately 90 degrees with orientation line of motion of said object, said 3D optical scanner orientation line forms approximately 45 degrees with said orientation line of said 2D optical scanner and orientation line of a plane light projector forms approximately 45 degrees with said orientation line of said 2D optical scanner.

\* \* \* \* \*